United States Patent [19]
Ebisawa

[11] Patent Number: 5,983,167
[45] Date of Patent: Nov. 9, 1999

[54] DISC DISHING MEASUREMENT METHOD AND APPARATUS

[75] Inventor: Shoei Ebisawa, Konosu, Japan

[73] Assignee: Dainippon Ink And Chemicals, Inc., Tokyo, Japan

[21] Appl. No.: 08/863,891

[22] Filed: May 28, 1997

[30] Foreign Application Priority Data

May 29, 1996 [JP] Japan ..................................... 8-134932

[51] Int. Cl.⁶ .................................................. G01B 11/24
[52] U.S. Cl. .......................................... 702/167; 702/155
[58] Field of Search .................................... 702/167, 172, 702/40, 155; 364/528.38; 59/603.1; 428/694; 369/44.32; 356/138; 250/559.45

[56] References Cited

U.S. PATENT DOCUMENTS

| | | | |
|---|---|---|---|
| 5,540,967 | 7/1996 | Toide et al. | 428/64.4 |
| 5,646,415 | 7/1997 | Yanagisawa | 250/559.45 |
| 5,684,778 | 11/1997 | Yamada et al. | 369/100 |
| 5,726,969 | 3/1998 | Moriya et al. | 369/275.1 |
| 5,815,255 | 9/1998 | Van Ochten et al. | 356/138 |

FOREIGN PATENT DOCUMENTS

| | | |
|---|---|---|
| 61-277007 | 12/1986 | Japan . |
| 62-120645 | 6/1987 | Japan . |
| 2-51009 | 2/1990 | Japan . |
| 3-69026 | 3/1991 | Japan . |

*Primary Examiner*—Marc S. Hoff
*Assistant Examiner*—Kendrick P. Patterson
*Attorney, Agent, or Firm*—Armstrong, Westerman, Hattori, McLeland & Naughton

[57] ABSTRACT

A method for measuring dishing in discs, including the steps of irradiating a laser beam along a scanning line which spirals from an inner side to an outer side of a surface of a magneto-optical disc or a digital video disc; determining a tilt angle at each of a plurality of measurement points on the scanning line based on displacement of a reflected laser beam from a normal reflected position; and using a measurement point on a first circuit on the inner side of the scanning line as a reference to determine dishing amounts at corresponding measurement points on circuits after the first circuit based on the tilt angles.

16 Claims, 5 Drawing Sheets

DISPLAY OF K=1

DISPLAY OF K=3

DISPLAY OF K=5

DISC DISHING MEASUREMENT METHOD AND APPARATUS

BACKGROUND OF THE INVENTION

1. Field of the Invention

The present invention relates to the measurement of dishing and disc shape profiling of magneto-optical discs and digital video (or versatile) discs.

2. Description of the Related Art

As examples of conventional methods for measuring the tilt and dishing shape of discs having photoreflective surfaces such as magneto-optical discs and digital video discs, there are those wherein a laser beam is irradiated onto the surface being measured and the displacement of the reflected laser beam is measured by position detection means.

Conventionally, the displacement from the regular reflection position which is that for the case in which the laser beam from the light source is perpendicularly incident on the measurement surface is measured, and the tilt is calculated from the relationships between this displacement and the geometrical distance between the reflection point and the light reception point.

Hereinbelow, a tilt measurement method according to the conventional art will be explained using the drawings.

FIG. 7 shows the case wherein no mechanical deformation, such as dishing or warping, is present on the disc which is the object of measurement, that is, the condition wherein a laser beam 5 is perpendicularly incident on the irradiated surface of the disc and is regularly reflected. In FIG. 7, 1 denotes laser beam emission means, 2 denotes a beam splitter, 3 denotes a disc which is an object of measurement and 4 denotes position detection means. Additionally, the distance between the reflective surface of the beam splitter 2 and the position detection means 4 is denoted $L_A$, and the distance between the reflective surface of the beam splitter 2 and the irradiated surface of the disc 3 is denoted $L_B$.

FIG. 8 shows the case wherein the surface of the disc 3 irradiated by the laser beam 5 is tilted by an angle θ with respect to a reference plane (the plane assuming that the laser beam 5 is perpendicularly incident, illustrated by the dashed line). This tilt θ is caused by mechanical deformations such as dishing and warping of the disc 3. A simple geometrical analysis will show that when the tilt of the disc has an angle θ with respect to the reference plane, the laser beam 5 will be reflected at an angle equal to two times θ with respect to the reference plane.

The path of the laser beam 5 which has been reflected and returned is changed by approximately 90 degrees by the beam splitter 2 and is incident on the light receiving surface of the position detection means 4.

When the position of the incident reflected beam is displaced from the regular reflection position, the position detection means 4 outputs a voltage having a value proportional to the displacement.

When the displacement X of the reflected laser beam is specified by the output voltage of the position detection means 4, the tilt (dishing) angle of the irradiated surface is generally defined to be 2θ, and is determined by the following equation.

$$2\theta = \arctan\frac{X}{L_A + L_B} \qquad (1)$$

Generally, the value of 2θ is measured over the entire surface of the disc, and the maximum value is defined to be the tilt. The angle θ represents the actual angle by which the disc is tilted with respect to the reference plane. Alternatively, if 2θ in equation (1) is given in radians and $(L_A+L_B)>>X$, then there is no problem in using the approximation $2\theta=(X/(L_A+L_B))$ for practical purposes.

In order to measure the tilt 2θ over the entire area of the disc 3, the relative positions of the laser beam emission means 1 and the position detection means 4 shown in FIG. 7 are fixed, and the output of the position detection means 4 is continuously read or recorded while the incident position of the laser beam 5 is moved along the radial direction of the disc 3 while rotating the disc 3.

The above-mentioned relative movement method allows the entire surface of a disc to be scanned, for example, by affixing a laser beam emission means and a position detection means and providing a mechanism for moving a disc horizontally while rotating. Alternatively, it is possible to have the disc be stationary and simply rotating, while the laser beam emission means and the position detection means are moved along the radial direction of the disc. As another method, a method for measuring the dishing of a disc based on the static electricity capacity may be considered, but this method has a drawback in that measurements must be made while precisely tracing the grooves contained in the photoreflective recording layer, so that an extremely long time is required. This drawback is apparent when in-line inspections are performed during continuous production, especially when complete inspections are performed.

As examples of methods for displaying the results obtained by these methods, there are methods wherein time is represented by a horizontal axis and the change in the output voltage from the position detection means 4 is simply displayed over time; alternatively, there are methods wherein the tilt is calculated from the dimensional constants determined by the geometrical arrangement of the disc 3 and the position detection means 4, and a variable representing the position on the disc such as the angle or the position along the circumferential direction is represented by the horizontal axis while the tilt is represented by the vertical axis.

However, even with these methods, there are problems in that the measurement results do not allow for a direct grasp on what type of shape the disc actually has and which parts are warped in which direction.

This is considered to be due to the fact that the physical quantities obtained by the measurements are the abstract quantities of "angles", and are no more than the enumeration of data for each point on the disc surface.

In consideration of these situations, the subject of the present invention is to offer a method and device for measuring the dishing of discs based on the tilt data of the discs, and further to offer a method and device which determines their approximate three-dimensional shapes by means of numerical operations and provides displays thereof.

SUMMARY OF THE INVENTION

In most cases, the warps and deformations in discs which are currently manufactured are large on the outer portions of the discs and become relatively smaller towards the inner portions, and this tendency has become especially apparent as the disc manufacturing art has improved over the years and the absolute values of the disc deformations have become smaller. Focusing on this fact, the present inventors have discovered that the amount of dishing and the dishing shape of a disc can be obtained by making the inner circumferential side of the disc as a reference and determining the amount of dishing at positions further out from this reference position based on the tilt of each position, and performing this procedure at numerous points on the surface of the disc.

That is, the present invention includes a method for measuring dishing amounts in discs, comprising irradiating a laser beam along a scanning line which spirals from an inner side to an outer side of a surface of a magneto-optical disc or a digital video disc; determining a tilt angle at each of a plurality of measurement points on the scanning line based on displacement of a reflected laser mean (reflected from the data recording layer of the disc) from a normal reflected position; and using a measurement point on a first circuit on the inner side of the scanning line as a reference to determine dishing amounts at corresponding measurement points on circuits after the first circuit based on the tilt angles.

While the first circuit of the scanning line should optimally be used as a single circuit on the inner side which is the reference for dishing, it is also possible to use the second or subsequent circuits depending on the state of dishing. When the first circuit is used as the reference, a plane which contains a starting point of said scanning line and perpendicularly intersects the emitted laser beam is taken as a reference plane, measurement points on the first circuit of the scanning line are assumed to lie on the reference plane, dishing amounts at measurement points on a (n+1)-th circuit of the spiral scanning line are sequentially determined based on said tilt angles with the n-th (wherein n=1, 2, 3, . . . , N) circuit as a reference, and these dishing amounts are summed from an inner side on the same normal line of the disc to determine a dishing amount from the reference plane.

With the method for measuring dishing in discs according to the present invention, the dishing can be measured more precisely if there is a large number of measurement points, but on the other hand, this increases the amount of time required for measurement. Therefore, the number of circuits of the scanning line of the laser beam and the number of the plurality of measurement points on said scanning line are set to be minimum numbers which permit the degree of dishing on the disc to be viewed three-dimensionally on a two-dimensional coordinate plane.

Specifically, the movement pitch for each circuit of the scanning line is within the range of 0.5–3 mm, and the number of measurement points on each circuit of the scanning line is within the range of 50–300. If the movement pitch is less than 0.5 mm, the number of circuits becomes too large and the measurement time is made longer; if the movement pitch exceeds 3 mm, the number of circuits becomes too small and it becomes difficult to obtain a display which accurately approximates the disc shape profile. Additionally, if the number of measurement points is less than 50, then the small number of measurement points makes it difficult to obtain a display which accurately approximates the disc shape profile; on the other hand, if the number exceeds 300, then the number of measurement points becomes too large and the measurement time becomes longer.

In order to scan a laser beam in a spiral across the surface of the disc, the disc should be rotated while relatively moving the irradiating position of the laser beam in the radial direction from the inner side toward the outer side of the surface of the disc. More specifically, either (1) the irradiating position of the laser beam can be moved in a radial direction form the inner side toward the outer side of the disc while holding the rotational position of the disc fixed, or (2) the disc can be moved so that the irradiating position of the laser beam moves in a radial direction from the inner side toward the outer side of the disc while holding the position of the emission source of the laser beam fixed.

At this time, the number of rotations of the disc should be within the range of 550–1600 rpm which is identical to the rotational speed at which the disc is actually used. Since the memory areas of digital video discs are in the range of the radius r=23–58 mm, and uses a CLV format (constant-speed-controlled format) employed at either 3.5 m/sec or 3.8 m/sec during play, the maximum rotation speed $N_{max}$ and the minimum rotation speed $N_{min}$ are respectively:

$N_{max}$=3.8 (m/sec)/(2×23×10$^{-3}$)×60=1578 rpm $N_{min}$=3.5 (m/sec)/(2×58×10$^{-3}$)×60=576 rpm Additionally, the time over which the irradiating position of the laser beam moves in the radial direction from an inner side to an outer side of a disc should be within the range of 0.5–3 seconds. If less than 0.5 seconds, the movement time becomes too fast and it becomes difficult to conduct proper measurements. Additionally, if more then 3 seconds, when disc production processes are introduced into the measurement method, there is a risk of delaying the production rate.

With the present invention, it is possible to use laminated type magneto-optical discs or digital video discs having recording layers on both the front and reverse surfaces, and to measure dishing amounts of both the front and reverse surfaces of the discs by irradiating laser beams on both the front and reverse surfaces. As a method thereof, it is possible to use only a single laser beam to take measurements on only one surface of the disc, then flipping it over to take measurements on the other surface so as to measure the dishing on the front and reverse surfaces consecutively, but preferably, a laser beam should be provided for each surface of the disc so as to simultaneously take measurements on the front and reverse surfaces. This applies not only to measurement of dishing, but also to cases of the other methods mentioned below.

The dishing can be displayed three-dimensionally on a two-dimensional coordinate plane by continuously connecting the measurement points along said scanning line based on displacement of said measurement points from said reference plane. The dishing display can be made to display not only the dishing on one surface, but also on both the front and reverse surfaces, by using a laminated type disc having recording layers on both the front and reverse surfaces as the magneto-optical disc or digital video disc, and determining the dishing on both surfaces by irradiating both the front surface and reverse surface with a laser beam.

While the method for measuring dishing according to the present invention can be worked independently by itself, it can also be incorporated into processes for manufacturing magneto-optical discs or digital video discs. Specifically, the present invention offers a continuous method for producing discs; comprising (1) a step of continuously producing magneto-optical discs or digital video discs; (2) a step of irradiating a laser beam along a scanning line which spirals from an inner side to an outer side of a surface of a magneto-optical disc or a digital video disc, determining a tilt angle at each of a plurality of measurement points on said scanning line based on displacement of a reflected laser beam from a normal reflected position, and using a measurement point on a first circuit on the inner side of the scanning line as a reference to determine dishing amounts at corresponding measurement points on circuits after the first circuit based on the tilt angles; (3) a step of disposing of discs wherein the tilt angle exceeds a threshold; and (4) a step of displaying the dishing three-dimensionally on a two-dimensional coordinate plane by continuously connecting the measurement points along the scanning line based on displacement of the measurement points from the reference plane.

As the processes for continuously producing magneto-optical discs or digital video discs, it is possible to use conventional methods.

When the maximum value of the tilt for all measurement points on the photoreflective surface of a disc being inspected is greater than or equal to a regulation angle, then it can be judged to be a defective product. In the case of a digital video disc, those wherein the tilt $\geq 0.8°$ in the radial direction of the disc are generally considered to be defective products. When the higher product quality is required, then those wherein the tilt $\geq 0.3°$ in the radial direction of the disc can be disposed of as defective products. Of course, when disposing of defective products, it is possible to use not only the tilt angle, but also the dishing amounts.

In the above manufacturing methods as well, laminated type magneto-optical discs or digital video discs having recording layers on both the front and reverse surfaces can be used, dishing amounts of both the front and reverse surfaces of the discs can be measured by irradiating laser beams on both the front and reverse surfaces, and the dishing amounts on both the front and reverse surfaces of the discs can be displayed.

The method for measuring dishing amounts in the discs according to the present invention can be achieved by an apparatus for measuring dishing in discs, comprising:

a displacement measuring device having laser beam emission means for irradiating a laser beam onto a surface of a magneto-optical disc or a digital video disc, and displacement sensing means for sensing displacement of a reflected beam of the laser beam from a normal reflected positions;

disc rotation means; and movement means for relatively moving the displacement measuring device and the disc rotation means in a radial direction of the disc;

wherein a laser beam is shined along a scanning line which spirals from an inner side to an outer side of a surface of a magneto-optical disc or digital video disc, a tilt angle at each of a plurality of measurement points on the scanning line is determined based on displacement of the reflected laser beam from the normal reflected position, and a measurement point on a first circuit on the inner side of the scanning line is used as a reference to determine dishing amounts at corresponding measurement points on circuits after the first circuit based on said tilt angles.

With the present invention described above, the magneto-optical discs or digital video discs can have two disc substrates which are laminated together by adhesion using ultraviolet-curable compounds which are cured due to irradiation by ultraviolet rays, and the ultraviolet irradiation can be performed by flash irradiation from at least one side of the discs. Flash irradiation allows the adhesive to be ultraviolet-cured while suppressing the expended electrical power in comparison to continuous irradiation, in other words, with less light than is required to cure the ultraviolet-curable compound with continuous irradiation. Consequently, ultraviolet irradiation allows large increases in the adhesive curing procedure per unit time. Furthermore, the degree of dishing can be decreased from the case of continuous irradiation which increases the expended electrical power.

As a subject of product quality control of digital video discs, aside from the dishing explained above, there is the thickness of the adhesive layer when two disc substrates are laminated together. This is due to the fact that if there are variation in the thickness of the adhesive layer, this causes variations in the thickness of the disc overall; and if this value exceeds the regulation range, then the characteristics of the disc will be degraded. However, since the adhesive layer is sandwiched between two disc substrates, they cannot be directly contacted, and they are not easily measured. For example, with ultrasonic flaw detection methods which are known as non-breakage inspection methods, it is difficult to measure the thickness of the adhesive layer of a disc which is only a few tens of microns thick. Even if this were possible, the inspection device would be extremely expensive, and the measurement time would be on the order of several minutes, which is not practical. Additionally, laser-focus displacement measuring devices which are known as another type of non-breakage inspection device require the object of measurement to be a transparent body, and therefore cannot be applied.

As explained above, the thickness of the adhesive layer between the disc substrates can be measured by applying the method for measuring dishing amounts in discs.

That is, the thickness between the photoreflective surfaces can be found by irradiating laser beams along scanning lines which spiral from an inner side to an outer side of both a front and reverse surface of a magneto-optical disc or a digital video disc and determining displacements from normal reflected positions of the laser beams; defining planes containing the starting points of said scanning lines and perpendicularly intersecting the irradiated laser beam as reference planes $Z_1$ and $Z_2$; making an assumption that the range of the first circuits of said scanning lines lie on said reference planes; sequentially determining dishing amounts on the (n+1)-th of said scanning lines based on said displacements with the n-th (wherein n=1, 2, 3, . . . , N) circuits as references; determining dishing amounts $T_{Z1}$ and $T_{Z2}$ of the disc with respect to the reference planes $Z_1$ and $Z_2$ set for the front and reverse surfaces by adding the dishing amounts of points from the inner side of the disc lying on the same normal line; and determining the value of $|T_{Z1}-T_{Z2}|$ for these dishing amounts $T_{Z1}$ and $T_{Z2}$. If the adhesive layer is present between the photoreflective surfaces, that is, between the recording layers, then this allows measurement of the thickness of the adhesive layer.

The above-mentioned method for measuring the thickness of a disc can measure both discs wherein the photoreflective layers are formed on the outermost front and reverse surfaces, and discs having laminated structures wherein layers composed of light transmitting materials are formed on the outermost front and reverse surfaces, and layers composed of photoreflective materials are formed underneath. As the former type of disc, there are two types; that is, discs composted of only photoreflective materials, and discs of laminated structures having surface layers composed of photoreflective materials on the outermost front and reverse surfaces, and having an intermediary layer composed of another type of material between these layers.

Additionally, the above-mentioned methods for measuring the thickness of discs naturally is capable of measuring the distance between photoreflective surfaces as the thickness of the disc, but it is also capable of measuring the thickness of an intermediary layer in discs of laminated structures having surface layers composed of photoreflective materials on the outermost front and reverse surfaces, an having an intermediary layer composed of another type of material between these layers. The measurement of the thickness of adhesive layers in digital video discs is one of these types of embodiments.

DETAILED DESCRIPTION OF THE PREFERRED EMBODIMENTS

Hereinbelow, the present invention shall be described based on embodiments thereof.

1. Dishing Amount Measurement Method

Figure 1:
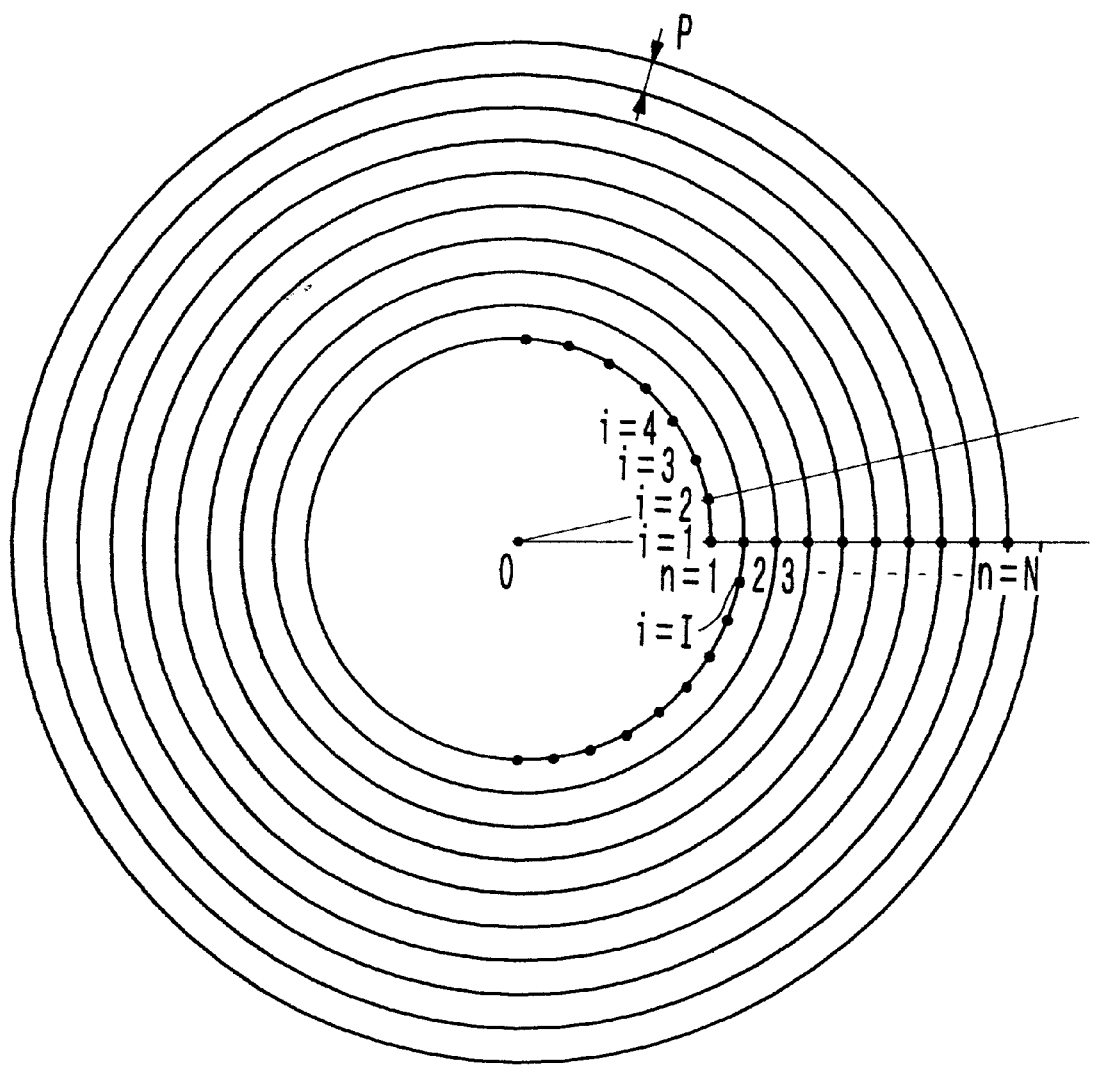
FIG. 1 is a diagram showing spiral scanning lines of a laser beam.

As shown in FIG. 1, the laser beam spot is irradiated on a disc along an imaginary spiral scanning line. This scanning line should preferably not precisely trace the recording grooves contained in the photoreflective surface, and the spiral scanning line should be made so as to be spaced wider than the spacing between the actual grooves (pitch). Here, the number of data points extracted from a single rotation of the disc is denoted by I and the distance by which the laser beam spot moves in the radial direction of the disc per rotation of the disc (hereinafter referred to as the movement pitch) is denoted by p.

The spiral scanning lines are numbered 1, 2, 3, ... from the inside, and the scanning line for the outermost circuit is denoted N. The origin of the spiral scanning line 1 begins to collect data at the point n=1, i=1 in FIG. 1, and the terminus of the spiral scanning line 1 is the origin of the spiral scanning line 2. Data are collected at I points at equidistant intervals for each circuit. The spacing between adjacent spiral scanning lines corresponds to the movement pitch p.

The method for determining the dishing amounts of a disc based on the collected data is as follows. The dishing amounts at the position of the spiral scanning line 1 are ignored for the sake of convenience, and it is assumed that the area to the inside of the scanning line 1 is a flat plane, in other words, that the dishing amount is zero. Then, the plane that perpendicularly intersects the laser beam containing the origin of the scanning line 1 is made the reference plane for the dishing amounts. As mentioned above, this assumption does not result in any problems for all practical purposes.

Dishing which faces upward with respect to the reference plane is considered to be positive, and dishing which faces downward is considered to be negative.

Figure 2:
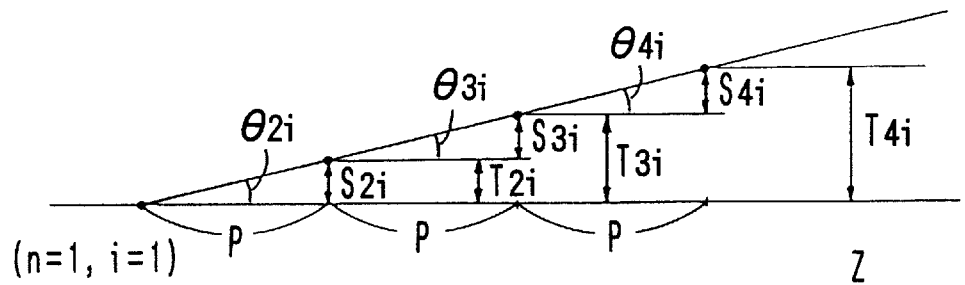
FIG. 2 is a diagram explaining the method for determining dishing of a disc according to the method of the present invention.

The displacement of the reflected laser beam at the i-th position on spiral scanning line n is denotes as $X_{ni}$ (wherein n=1, 2, ..., N and i=1, 2, ..., I). $X_{1i}, X_{2i}, ..., X_{ni}, X_{Nni}$ may be considered to be data collected from approximately the same normal line. Then, as mentioned above, by ignoring the dishing amounts on the spiral scanning line 1 for convenience and assuming that the area inside the spiral scanning line 1 is a flat plane, then the dishing amounts at the i-th position on spiral scanning line 2 (denoted $S_{2i}$, for convenience) can be expressed as a first-order approximation using $X_{1i}$ as demonstrated in FIG. 2, by the following:

$$S_{2i} = p \tan \theta_{2i} \quad (2)$$

$$\theta_{2i} = \frac{1}{2} \arctan\left(\frac{X_{2i}}{L_A + L_B}\right) \quad (3)$$

More generally, by changing the suffix "2" in the above equations to "n", the displacement $X_{ni}$ of the reflected laser beam extracted at an arbitrary i-th position on an arbitrary spiral scanning line n allows the dishing $S_{ni}$ at the i-th position on the next adjacent spiral scanning line (n+1) to be expressed with reference to that position.

Taking a reference plane Z which perpendicularly intersects the incident laser beam and contains the predetermined position on the inner side of the disc at which data collection is started, for example, the position at which the data $X_{11}$ is extracted, the dishing amounts $T_{ni}$ from the reference plane Z at an arbitrary position on the spiral scanning line can be determined by the following equation which sums the values from the inner side of the disc.

$$T_{ni} = \sum_{j=1}^{n} S_{ji} \quad (4)$$

While a method for determining the dish on one surface of the disc has been explained above, it is also possible to simultaneously determine the dishing amounts on the opposite surface by simultaneously irradiating a laser beam over both surfaces of the disc.

2. Disc Shape Profiling Method

In order to display a disc shape profile, the following procedure is performed. That is, the spiral scanning lines which the laser beam traces on the reference plane are displayed in roughly elliptical shapes, and the distance $T_{ni}$ of each measurement point with respect to the reference plane is added to they component in the equation for an ellipse. That is, it is expressed by the following equation.

$$x_{ni} = \left(a + np + \frac{360\,pi}{I}\right)\sin\left(\frac{360i}{I}\right) \quad (5)$$

$$y_{ni} = kT_{ni} + \left(b + np + \frac{360pi}{I}\right)\cos\left(\frac{360i}{I}\right)$$

By sequentially joining the coordinates $(x_{ni}, y_{ni})$ determined by the above equation with straight lines, the disc shape profile can be displayed on a two-dimensional coordinate plane such as to be capable of being viewed three-dimensionally. The coordinates $(x_{ni}, y_{ni})$ are joined together in order by first changing i from 1 to I with n=1, then joining the points with i from 1 to I with n=2. This operation is repeated until n=N.

In equation (5), a and b denote the lengths of the major and minor axes for expressing the spiral scanning line 1 (innermost circuit) as a rough ellipse, $T_{ni}$ denotes the value determined by equation (4), p denotes the movement pitch, and I denotes the number of data points collected per rotation of the disc. While the value of I is decided by the required measurement precision, if the value of I is too small, the rough ellipse formed by connecting the coordinates ($x_{ni}$, $y_{ni}$) is not smooth and becomes bumpy; therefore it is preferable that I≧50.

Additionally, k is a coefficient for adjusting the sensitivity or degree of exaggeration when displaying the disc shape profile in a three-dimensionally viewable manner (hereinbelow, k shall simply be referred to as the exaggeration coefficient), and the larger this value is made, the greater the dishing will seem on the display even if the dishing is only slight.

3. Thickness Measurement Method

Figure 3:
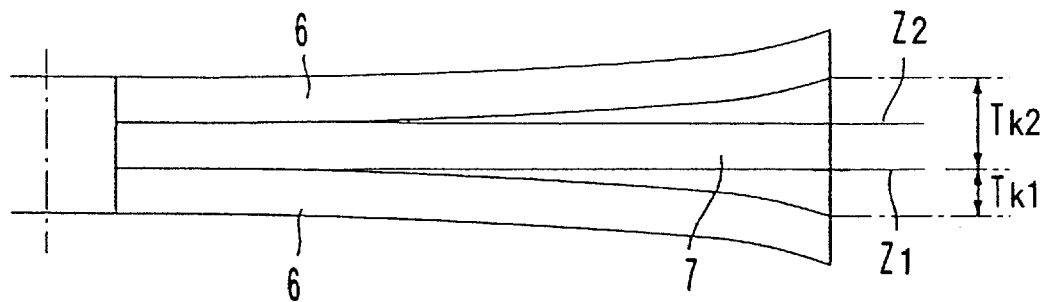
FIG. 3 is a diagram showing an embodiment of the thickness measuring method of the present invention.

Next, an example of a thickness measurement method for determining the thickness of the intermediary layer of a disc based on the measured dishing amounts shall be explained with reference to FIG. 3. FIG. 3 schematically illustrates the cross section of a disc having an intermediary layer 7 composed of adhesives between photoreflective layers 6, 6 which are recording layers; in actuality, the thickness of a photoreflective layer 6 is extremely small in comparison to the intermediary layer 7.

One of the reference planes $Z_1$ and $Z_2$, which are respectively set for the front and reverse surfaces of the disc, is taken as a common reference plane K (in this example, reference plane $Z_1$ is employed), and the dishing on the front surface side of the disc is taken as $T_{K2}$ (determined by the above-mentioned dishing amount measurement method). The dishing amounts at the position corresponding to dishing amounts $T_{K2}$ on the reverse surface is defined as $T_1$, and assuming that the thickness of the photoreflective layer 6 is constant, then the thickness of T of the intermediary layer 7 at that position can be determined by the following equation.

$$T = T_{K2} - T_{K1} \quad (6)$$

By performing the above procedure for all of the data points at which the dishing amounts have been determined, the maximum intermediary layer 7 for a single disc, that is, the thickness $T_{max}$ of the adhesive layer, can be determined. Then, if $T_{max}$ exceeds a standard control value, this disc may be considered to be a defect.

In the above embodiment, one of the reference planes respectively set for the front and reverse of a disc was taken as a common reference plane; however, it is also possible to set a separate new common reference plane. For example, the plane containing the middle points between the front and reverse reference planes may be made into a reference plane.

Figure 4:
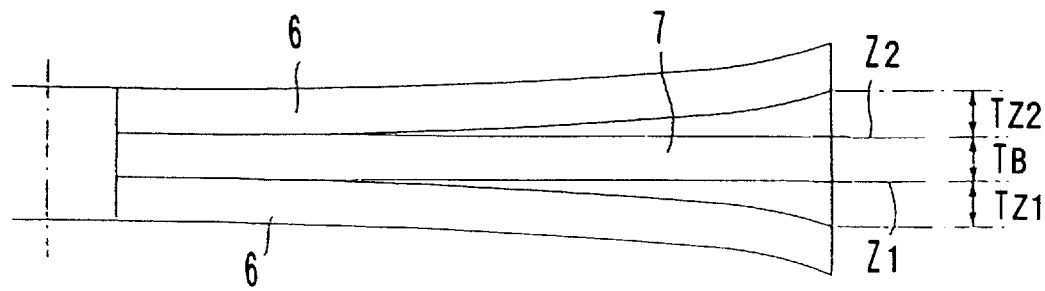
FIG. 4 is a diagram showing another example of a thickness measuring process according to the present invention.

Additionally, while the thickness of the intermediary layer 7 is measured by setting a common reference plane for the above-mentioned embodiment, the measurements may be made without setting a common reference plane. For example, as shown in FIG. 4, the thickness of the intermediary layer 7 can be measured by using the dishing amounts $T_{Z1}$ and $T_{Z2}$ based on the reference planes $Z_1$ and $Z_2$ respectively set for the front and reverse surfaces together with the distance $T_B$ between the reference planes $Z_1$ and $Z_2$, according to the following equation:

$$T = T_{Z2} - T_{Z1} + T_B \quad (7)$$

4. Embodiments of Measuring Device

Figure 5:
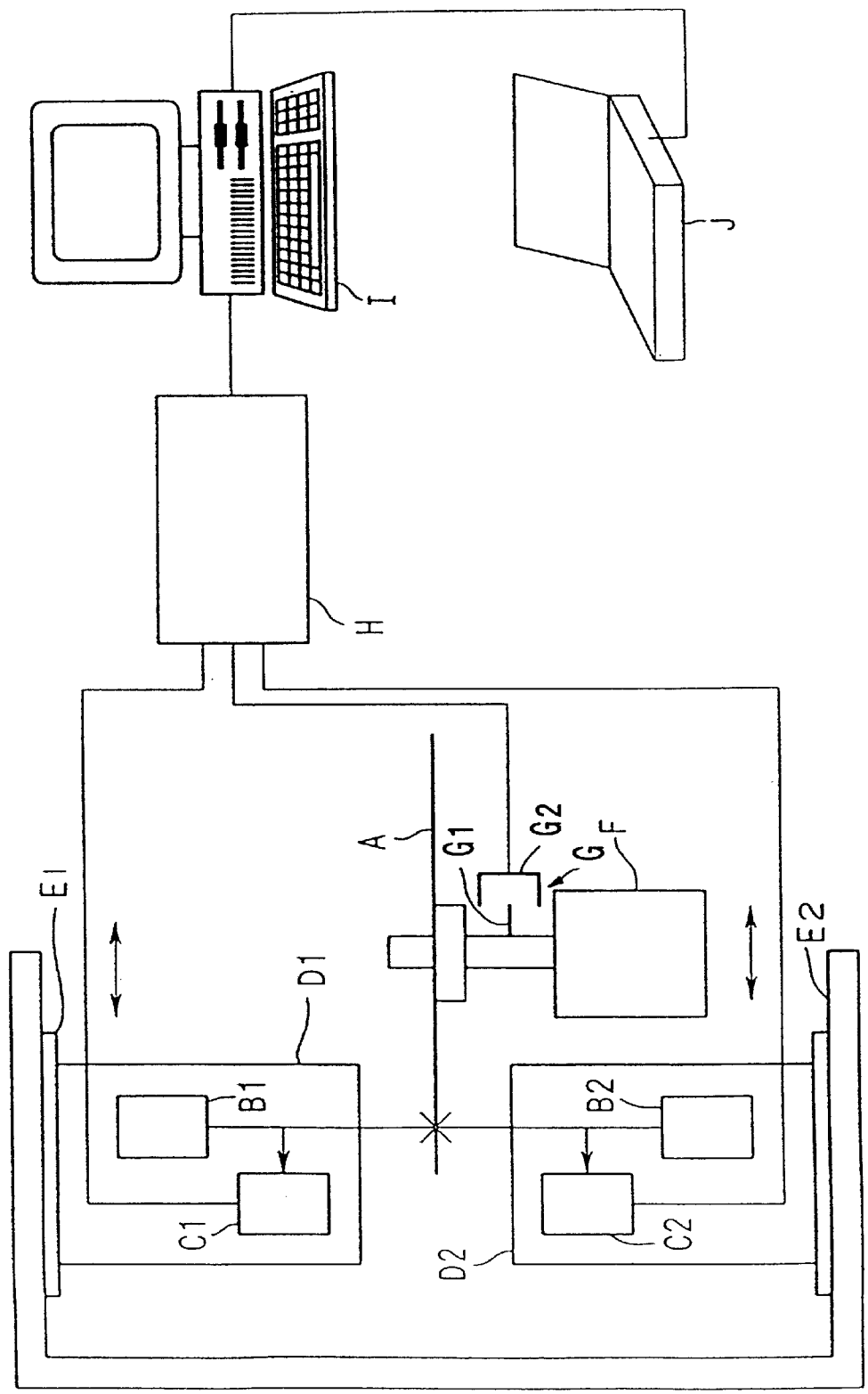
FIG. 5 is a block diagram showing an embodiment of a measuring device according to the present invention.

FIG. 5 is a schematic illustration of one embodiment of the measuring device of the present invention. In the present embodiment, a pair of displacement measuring devices D1 and D2 are provided so as to be capable of measuring the dishing on both the front and reverse surfaces of a disc.

In FIG. 5, B1 and B2 denote laser beam emission means. In order to make the measurement errors smaller, the beam diameter used for laser beam irradiation should preferably be small, 1.5 mm or less, or the device should have a mechanism for adjusting the beam diameter at the reflected beam receiving position.

C1 and C2 denote position sensing means for receiving light from the laser beams reflected from the disc A. As these position sensing means, it is possible to use position sensitive devices (PSDs) which are commonly known and used. While there are both one-dimensional and two-dimensional types of PSDs, the appropriate type should be chosen according to the purpose. For example, when only determining the tilt for arbitrary points along only one direction, either the radial direction of the disc or the circumferential direction of the disc, the PSD may be of the one-dimensional type. Additionally, a one-dimensional type may be used to determine only the tilt along the radial direction of the disc, then the tilt along the circumferential direction of the disc can be approximated from that value. However, in order to measure in both the radial and circumferential directions of the disc simultaneously and/or at high speed, a two-dimensional type may be used. A two-dimensional type should most preferably be used when measurements are performed in-line during a continuous manufacturing process for laminated discs.

Additionally, displacement data of the reflected laser beam are outputted from these position sensing means C1 and C2.

The laser beam emission means B1 and position sensing means C1 are affixed, and the laser beam emission means B2 and position sensing means C2 are affixed so that their mutual positions are held unchanged, thereby forming the displacement measuring devices D1 and D2. Movement means E for moving these displacement measuring devices D1 and D2 relative to the disc A in the radial direction of the disc A are provided. As the movement means, it is possible to use uniaxial electromotive sliders which are commonly known and used, or other types thereof.

F denotes rotation means for rotating the disc A, for which an AC motor having little dispersion in the rotational speed should preferably be used. In the present invention, since the tilt measurements are not made by tracing grooves, there is no need for the rotational speed of the rotation means of the disc to change between the measurement points on the inner side and outer side, so that the rotational speed of a disc during measurement of a single disc may be kept constant.

While FIG. 5 shows an embodiment wherein the disc is rotated but held stationary in the radial direction, and only the displacement measuring devices are moved, it is possible to hold only the displacement measuring devices stationary and move the disc along the radial direction while rotating.

G denotes rotational position sensing means for sensing the rotational position of the disc A. For example, it is possible to use a method for generating rotational pulses wherein a shielding part G1 sufficient to shield light is attached to the axle for rotating the disc, and a commonly known and used photo-interruptor element G2 can be used to detect the shielding part G1 has passed.

As data recording means H for collecting the reflected laser beam displacement data from the position sensing means C1 and C2 and the rotational position data from the rotational position sensing mean G at uniform intervals of time and recording these data, it is possible to use a mechanism having an A/D converter and an electronic memory together. As a commonly known and used device having this type of mechanism, there is the model "ADM-652T" manufactured by Microscience Corporation, capable of being used on an ISA bus.

I denotes a processing means for setting the reference planes $Z_1$ and $Z_2$ for the front and reverse surfaces of the discs based on reflected laser beam displacement data, and for determining the dishing amounts $T_{Z1}$ and $T_{Z2}$ with respect to the reference planes $Z_1$ and $Z_2$ at corresponding positions on the front and reverse of discs based on the rotational position data and the reflected laser beam displacement data. When the disc shape profile is to be displayed or a thickness measurement is to be made, then the processing means 1 can be used to perform operations such as the above-given equation (5) or the above-given $|T_{Z1}-T_{Z2}|$. As this processing means, it is possible to use a commonly known and used personal computer of almost any make and model.

Although the disc shape profile can be displayed at the processing means I, since personal computers often do not have sufficient processing power to simultaneously perform the above operations and the display, a personal computer should preferably be connected exclusively for the purposes of disc shape profiling, as disc shape profile display J.

The operations of the above-mentioned measuring device are as follows. That is, while rotating the disc A by the rotating means F, the laser beams irradiated on the surfaces of the disc A from the displacement measuring devices D1 and D2 are moved in the radial direction within the photo-reflective plane of the disc A. At this time, the change in the displacement of the reflected beam due to the dishing of the disc A in the radial direction is continuously stored in the data recording means H in correspondence with the rotational angle of the disc A. After the entire surface of the disc has been scanned, the stored data are withdrawn and processed by the processing means During the above-mentioned operations, when the rotational speed of the disc and the periods between the data recordings are constant, the number of data points collected from the position sensing means C1 and C2 per rotation of the disc is constant. Additionally, the displacement of the reflected beams can easily be stored in correspondence with the rotational angles of the disc A if the data from the position sensing means C1 and C2 are taken as timing signals for starting data collection, and using a rotating pulse generated by a commonly known and used photo-interruptor element or the like.

5. Example of Disc Surface Profile Display

An example of the display of a disc shape profile will be explained below. The object of measurement was a magneto-optical disc (120 mm in diameter) of which only one side was measured.

The range of measurement of the dishing was from a position at 47 mm along the diameter to a position at 116 mm along the diameter on the surface at the side having a data recording layer.

With the device shown in FIG. 5, the rotational speed of the disc A was made constant at 12 rotations per second, the data collection interval of the position sensing means C1 was made 833 μsec, and the movement pitch of the displacement measuring device D1 was made p=1.08 mm, as a result of which the number of data points per rotation of the disc was I=100 and the number of circuits of the scanning line was 32. Accordingly, in the present example, the total number of measured data points to be processed was 3200.

Next, FIG. 6 shows displays of disc shape profiles made to be three-dimensionally viewable using the methods of the present invention. The displacement $T_{ni}$ from the reference plane was determined in μm units, and the numerical values were added by equation (5). The graphics were displayed on a personal computer wherein the entire screen was scaled by 1400 in the horizontal direction and 1050 in the vertical direction, and the lengths of the major axes of the innermost ellipse and outermost ellipse were respectively 160 and 500, while the lengths of the minor axes were 90 and 281.

Figure 6A:
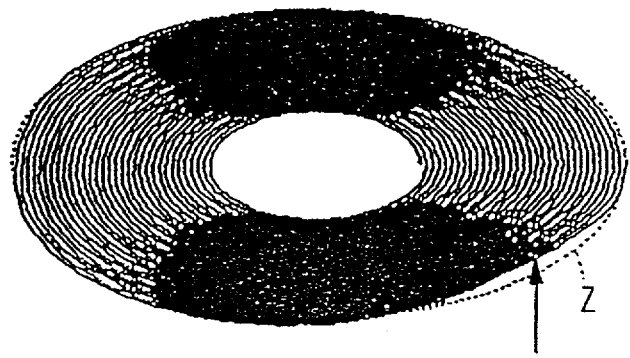
FIGS. 6(a)–6(c) are diagrams showing examples for displaying a disc shape profile three-dimensionally on a two-dimensional coordinate plane according to the present invention.
Figure 6B:
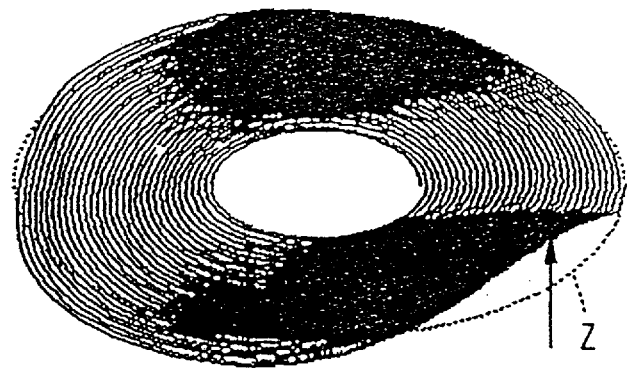
Figure 6C:
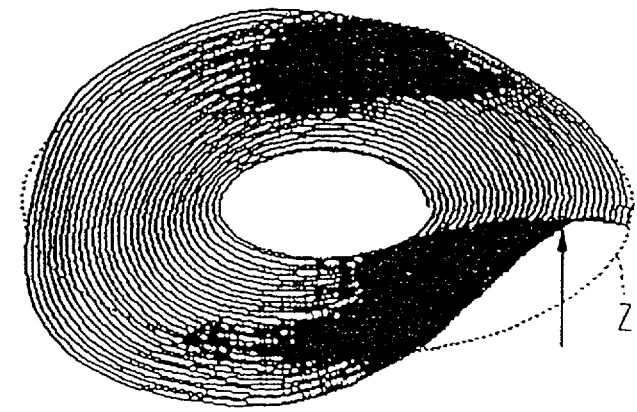
Figure 7:
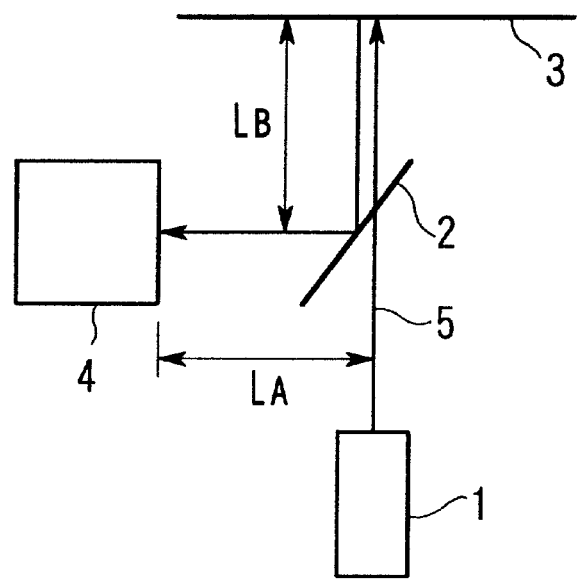
FIG. 7 is a diagram showing an example of a conventional tilt measuring method.
Figure 8:
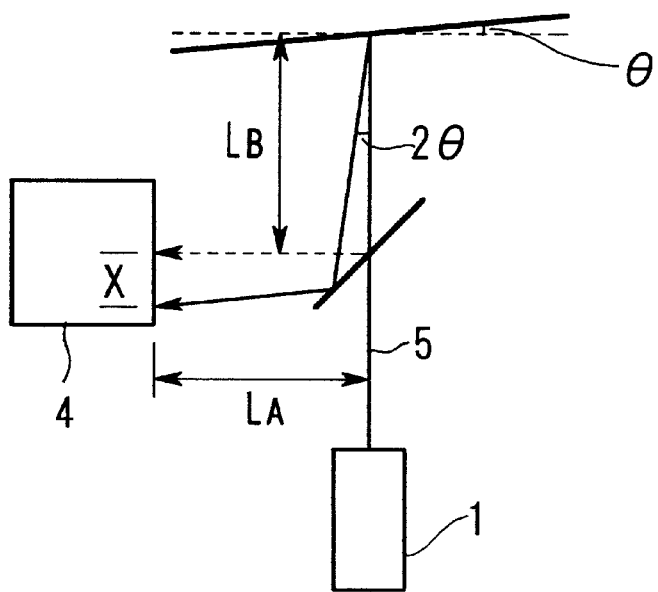
FIG. 8 is a diagram showing a case wherein the reflected laser beam is displaced when the disc which is the object of measurement in FIG. 7 has dishing.

FIG. 6(a) shows the case wherein the exaggeration coefficient k=1, FIG. 6(b) the case of k=3, and FIG. 6(c) the case of k=5. The data on which the calculations were based are the same for all cases (a) through (c). In the drawing, the position indicated by the arrow denotes the point at which the dishing amounts from the reference plane is maximum. While the dishing was numerically only a slight 50 μm at the maximum point, it can be seen that the dishing becomes more clearly expressed as the value of the exaggeration coefficient k increases.

In the present display method, the shapes of the ellipses themselves change due to the initial selection of the coordinate scale. Consequently, the value of k can also be considered to be relative.

As explained above, the present invention allows dishing amounts of discs to be easily determined based on numerical tilt data, and allows the dishing to be displayed as a disc shape profile.

I claim:

1. A method for measuring dishing amounts in discs, comprising the steps of:

irradiating a laser beam along a scanning line which spirals from an inner side to an outer side of a surface of a magneto-optical disc or a digital video disc;

determining a tilt angle at each of a plurality of measurement points on said scanning line based on displacement of a reflected laser beam from a normal reflected position; and using a measurement point on a first circuit on the inner side of said scanning line as a reference to determine dishing amounts at corresponding measurement points on circuits after said first circuit based on said tilt angles.

2. A method for measuring dishing amounts in discs in accordance with claim 1, wherein a plane which contains a starting point of said scanning line and perpendicularly intersects the emitted laser beam is taken as a reference plane, measurement points on the first circuit of said scanning line are assumed to lie on said reference plane, dishing amounts at measurement points on a (n+1)-th circuit of said spiral scanning line are sequentially determined based on said tilt angles with the n-th (wherein n=1, 2, 3, ..., N) circuit as a reference, and these dishing amounts are summed from an inner side on the same normal line of the disc to determine a dishing amount from said reference plane.

3. A method for measuring dishing amounts in discs in accordance with claim 1, wherein the number of circuits of the scanning line of the laser beam and the number of the plurality of measurement points on said scanning line are set to be minimum numbers which permit the degree of dishing amounts on the disc to be viewed three-dimensionally on a two-dimensional coordinate plane.

4. A method for measuring dishing amounts in discs in accordance with claim 1, wherein a movement pitch for each circuit of said scanning line is within the range of 0.5–3 mm, and the number of measurement points on each circuit of said scanning line is within the range of 50–300.

5. A method for measuring dishing amounts in discs in accordance with claim 1, wherein the position of irradiation of the laser beam is moved relatively in a radial direction from an inner side to an outer side of the surface of a disc, while rotating the disc.

6. A method for measuring dishing amounts in discs in accordance with claim 1, wherein the disc rotation is 550–1600 rpm, and the time over which the irradiated position of the laser beam moves in the radial direction from an inner side to an outer side of a disc is within the range of 0.5–3 seconds.

7. A method for measuring dishing amounts in discs in accordance with claim 1, wherein laminated type magneto-optical discs or digital video discs having recording layers on both the front and reverse surfaces are used, and dishing both the front and reverse surfaces of the discs are measured by irradiating laser beams on both the front and reverse surfaces.

8. A method for displaying disc shape profiles, comprising the steps of:

irradiating a laser beam along a scanning line which spirals from an inner side to an outer side of a surface of magneto-optical disc or a digital video disc;

determining a tilt angle at each of a plurality of measurement points on said scanning line based on displacement of a reflected laser beam from a normal reflected position;

using a measurement point on a first circuit on the inner side of said scanning line as a reference to determine dishing amounts at corresponding measurement points on circuits after said first circuit based on said tilt angles; and displaying the dishing three-dimensionally on a two-dimensional coordinate plane by continuously connecting the measurement points along said scanning line based on displacement of said measurement points from said reference plane.

9. A method for displaying disc shape profiles in accordance with claim 8, wherein laminated type magneto-optical discs or digital video discs having recording layers on both the front and reverse surfaces are used, and laser beams are irradiated on both the front and reverse surfaces.

10. A continuous method for producing discs, comprising the steps of:

(1) continuously producing magneto-optical discs or digital video discs;

(2) irradiating a laser beam along a scanning line which spirals from an inner side to an outer side of a surface of a magneto-optical disc or a digital video disc, determining a tilt angle at each of a plurality of measurement points on said scanning line based on displacement of a reflected laser beam from a normal reflected position, and using a measurement point on a first circuit on the inner side of said scanning line as a reference to determine dishing amounts at corresponding measurement points on circuits after said first circuit based on said tilt angles; and (3) disposing of discs when even any one of said tilt angles exceeds a threshold.

11. A continuous method for producing discs in accordance with claim 10, wherein laminated type magneto-optical discs or digital video discs having recording layers on both the front and reverse surfaces are used, and dishing amounts of both the front and reverse surfaces of the discs are measured by irradiating laser beams on both the front and reverse surfaces.

12. A continuous method for producing discs in accordance with claim 10, further comprising the step of displaying the dishing three-dimensionally on a two-dimensional coordinate plane by continuously connecting the measurement points along said scanning line based on displacement of said measurement points from said reference plane.

13. A continuous method for producing discs in accordance with claim 12, wherein the magneto-optical discs or digital video discs have two disc substrates which are laminated together by adhesion using ultraviolet-curable compounds which are cured due to irradiation by ultraviolet rays.

14. A continuous method for producing discs in accordance with claim 13, wherein the ultraviolet irradiation is performed by flash irradiation from at least one side of the discs.

15. An apparatus for measuring dishing amounts in discs, comprising:

a displacement measuring device having laser beam emission means for irradiating a laser beam onto a surface of a magneto-optical disc or a digital video disc, and displacement sensing means for sensing displacement of a reflected beam of the laser beam from a normal reflected positions;

disc rotation means; and movement means for relatively moving said displacement measuring device and said disc rotation means in a radial direction of said disc, wherein a laser beam is irradiated along a scanning line which spirals from an inner side to an outer side of a surface of a magneto-optical disc or digital video disc, a tilt angle at each of a plurality of measurement points on said scanning line is determined based on displacement of the reflected laser beam from the normal reflected position, and a measurement point on a first circuit on the inner side of said scanning line is used as a reference to determine dishing amounts at corresponding measurement points on circuits after said first circuit based on said tilt angles.

16. An apparatus for measuring dishing amounts in discs in accordance with claim 15, wherein laminated type magneto-optical discs or digital video discs having recording layers on both the front and reverse surfaces are used, and displacement measuring devices are provided on both the front and reverse sides thereof.

* * * * *